(12) United States Patent
Rus-Perez et al.

(10) Patent No.: US 7,928,374 B2
(45) Date of Patent: Apr. 19, 2011

(54) RESOLUTION IMPROVEMENT IN THE COUPLING OF PLANAR DIFFERENTIAL MOBILITY ANALYZERS WITH MASS SPECTROMETERS OR OTHER ANALYZERS AND DETECTORS

(75) Inventors: Juan Rus-Perez, Valladolid (ES); Juan Fernandez de la Mora, New Haven, CT (US)

(73) Assignee: Sociedad Europea de Analisis Diferencial de Movilidad, Madrid (ES)

( * ) Notice: Subject to any disclaimer, the term of this patent is extended or adjusted under 35 U.S.C. 154(b) by 121 days.

(21) Appl. No.: 11/786,688

(22) Filed: Apr. 11, 2007

(65) Prior Publication Data

US 2008/0251714 A1 Oct. 16, 2008

Related U.S. Application Data

(60) Provisional application No. 60/790,679, filed on Apr. 10, 2006.

(51) Int. Cl.
*H01J 49/02* (2006.01)
(52) U.S. Cl. ........ 250/292; 250/281; 250/282; 250/283; 250/290
(58) Field of Classification Search .................. 250/281, 250/282, 283, 290, 292
See application file for complete search history.

(56) References Cited

U.S. PATENT DOCUMENTS

| | | | | |
|---|---|---|---|---|
| 5,869,831 | A * | 2/1999 | De La Mora et al. | 250/288 |
| 5,936,242 | A * | 8/1999 | De La Mora et al. | 250/288 |
| 7,339,166 | B2 * | 3/2008 | Tang et al. | 250/288 |
| 7,521,673 | B2 * | 4/2009 | Arcas et al. | 250/294 |
| 2005/0045818 | A1 * | 3/2005 | De La Mora et al. | 250/294 |
| 2007/0272847 | A1 * | 11/2007 | Labowsky et al. | 250/283 |
| 2008/0121797 | A1 * | 5/2008 | Wu | 250/283 |
| 2008/0156978 | A1 * | 7/2008 | Shvartsburg et al. | 250/282 |

* cited by examiner

*Primary Examiner* — David A Vanore
*Assistant Examiner* — Michael Maskell
(74) *Attorney, Agent, or Firm* — Hoffmann & Baron, LLP

(57) ABSTRACT

Prior work on differential mobility analysis (DMA) combined with mass spectrometry (MS) has shown how to couple the output of the DMA with the inlet of an atmospheric pressure ionization mass spectrometer (APCI-MS). However, the conventional ion inlet to an APCI-MS is a round orifice, while conventional DMA geometries make use of elongated slits. The coupling of two systems with such different symmetries limits considerably the resolutions attainable by the DMA in a DMA-MS combination below the value of the DMA alone. The purpose of this invention is to overcome this limitation in the case of a parallel plate DMA. One solution involves use of an elongated rather than a circular MS sampling hole, with the long dimension of the MS inlet hole aligned with that of the DMA slit. Another involves use of a more elongated orifice in the DMA exit and a more circular hole on the MS inlet, the two being connected either through a short transfer conduit or through an ion guide. The DMAs described can also be coupled profitably to detectors and analyzers other than mass spectrometers.

15 Claims, 8 Drawing Sheets

RESOLUTION IMPROVEMENT IN THE COUPLING OF PLANAR DIFFERENTIAL MOBILITY ANALYZERS WITH MASS SPECTROMETERS OR OTHER ANALYZERS AND DETECTORS

CROSS REFERENCE TO RELATED APPLICATION

This application claims the benefit of priority to U.S. Provisional Patent Application No. US60/790,679, filed on Apr. 10, 2006.

REFERENCES

Ashkenas, W. and Sherman, F. S. (1966) In *Rarefied Gas Dynamics* (Edited by de Leeuw, J. H.). Academic, New York.

Fernández de la Mora, J. (1985) Surface impact of seeded free jets at relatively large background densities, J. Chem. Phys. 82, 3453-3464.

Fernández de la Mora J., S. V. Hering, N. Rao and P. McMurry (1990) Hypersonic Impaction of Ultrafine particles, J. Aerosol Sci., 21, 169-187.

Fernández de la Mora, J., L., de Juan, T. Eichler and J. Rosell (1999), Method and apparatus for separating ions in a gas for mass spectrometry; U.S. Pat. Nos. 5,869,831 (9 Feb. 1999) and 5,936,242 (10 Aug. 1999)

Fernández de la Mora J (2002) Diffusion broadening in converging differential mobility analyzers, J. Aerosol Science, 33, 411-437

Flagan, Richard C. and Zhang, Shou-Hua (1997), Radial differential mobility analyzer. U.S. Pat. Nos. 5,596,136 (Jan. 21, 1997) and 5,606,112 (Feb. 25, 1997).

Gamero-Castaño, M. and Fernandez de la Mora, A condensation nucleus counter (CNC) sensitive to singly charged subnanometer particles; J. Aerosol Sci., 31, 757-772 (2000).

Iribarne, Julio V. and Thomson, Bruce A. (1981) Method and apparatus for the analysis of chemical compounds in aqueous solution by mass spectroscopy of evaporating ions, U.S. Pat. No. 4,300,044, Nov. 10, 1981.

Labowsky; Michael J., Fenn; John B., Yamashita; Masamichi (1985) Method and apparatus for the mass spectrometric analysis of solutions, U.S. Pat. No. 4,531,056, Jul. 23, 1985

Labowsky M., and J. Fernandez de la Mora, Novel ion mobility analyzers and filters, J. Aerosol Science, 37(3) 340-362, 2006.

Labowsky, Michael J. and Juan Fernández de la Mora, Ion mobility separation devices, International Application published under the patent cooperation treaty (PCT); PCT publication WO2004/077016; PCT/US2004/005133; Sep. 10, 2004

Pourprix, M. (1992). Electrostatic detector of aerosol particles. U.S. Pat. No. 5,117,190.

Ude, S., PhD Thesis, Yale University, 2004.

Ude, Sven, Juan Fernández de la Mora and Bruce Thomson (2004), Charge -Induced Unfolding of Multiply Charged Polyethylene Glycol Ions Investigated via IMS-MS, paper presented at the 2004 annual meeting of the American Society for mass spectrometry.

Zhang, S. H., Akutsu, Y., Rusell, L. M., & Flagan, R. C. (1995). Radial Differential Mobility Analyzer. Aerosol Science and Technology, 23, 357-372.

Zhang, S. H., & Flagan, R. C. (1996). Resolution of the radial differential mobility analyzer for ultrafine particles. J. Aerosol Science, 27, 1179-1200.

FIELD OF THE INVENTION

This invention relates to the analysis of ions by mass spectrometry (MS). More specifically, it describes methods and devices to couple a MS with an analytical instrument referred to as a differential mobility analyzer (DMA), separating ions in space, and placed upstream of the MS. The invention overcomes the loss of DMA resolution resulting in prior art for DMA-MS coupling. The invention may be similarly used to couple a DMA to a second instrument other than a mass spectrometer, including a second DMA, one detector, or multiple detectors.

INTRODUCTION AND PRIOR ART

Ion mobility spectrometers (IMS) are instruments that separate ions in a gas according to their electrical mobility Z, defined as the ratio between the average drift velocity $u_d$ through the gas induced in the ion by a external electric field E, and the field itself: $Z=u_d/E$. Z depends on the charge on the ion and its shape, so that its measurement in a given gas at a given pressure and temperature provides specific information about the ion. An important characteristic of an IMS is its resolving power $R=Z/\Delta Z$, defined as the ratio of the peak width $\Delta Z$ (full width at half maximum, FWHM) over its mean mobility for an ion of sharply defined mobility. The resolving power of IMS systems can be as high as 100 (even larger under special circumstances), whereby they can separate ions with Z values differing by less than 1%. MS, separating ions according to their mass/charge ratio, is capable of much higher resolving power, but it is often desirable to increase this power further, as well as to reduce background noise and to separate ions with identical mass/charge ratio. This end can be served by combining an IMS in series with a MS. Most IMS-MS work has relied on IMS systems separating pulsed ion packets in time. This scheme has great analytical advantages, but it has required the development of complex systems coupling the IMS to the MS. This feature generally precludes the simpler use of commercial mass spectrometers, which have reached a level of reliability and sensitivity very difficult to match by specialized developments. For this reason, there is much interest in the development of IMS systems suitable to be coupled to a commercial MS with as few modifications as possible to the vacuum system of the MS itself.

The present invention is concerned principally with mass spectrometers of the atmospheric pressure ionization type (API-MS), where the ions to be analyzed are formed at relatively large pressures, often at atmospheric pressure or near it. Because MS analysis functions in a vacuum, there is a need to transfer these ions from a high to a low pressure, while minimizing the simultaneous transfer of neutral gas species. The first element in this ion transfer system is a small orifice, typically a few hundred microns in diameter, open on one side to the high-pressure region, and open on the other side to the first stage of the vacuum system. This orifice may be a hole drilled on a thin plate, a capillary tube, etc. It will generally be referred to here as the "inlet orifice" to the MS. It is important to note that in all existing API-MS systems this orifice is round. There are in fact important advantages to keeping round at least the vacuum end of the orifice, as this leads to the formation of an axisymmetric supersonic free jet, where axial symmetry simplifies the operations of sampling (skimming) the central portions of the jet into a second differentially pumped vacuum chamber, as well as the design of electrostatic or other focusing systems desirable to improve ion transmission efficiency.

We have noted the difficulty of coupling pulsed IMS systems to commercial API-MS. The coupling is much simpler in IMS devices where ions are separated in space rather than in time. Two fairly different such methods have been successfully demonstrated. One is termed Field Asymmetric IMS (FAIMS), and relies on slight nonlinearities in the relation between the drift velocity of the ion and the external electric field. The other method is called Differential Mobility Analysis (DMA), and combines a laminar flow field with an electric field. More specifically, for the purposes of this invention, a DMA is defined as an instrument combining (i) a large laminar flow field produced by a suitable laminarization system with (ii) an electric field generated by several conducting or semiconducting electrodes or grids charged at various points to various electrical potentials, while (iii) a narrow stream of ions with various electrical mobilities is injected into the large laminar flow through a narrow inlet orifice or slit with the help of either an electric field or a small flow of gas, (iv) these ions are separated in space according to their electrical mobility, whereby (v) ions of selected electrical mobilities reach one or several sampling or collecting devices. Both DMAs and FAIMS instruments can be operated as band-pass filters and transmit to the MS only a small selected class among all the ions ingested. This invention will be concerned with the DMA, which has much higher resolving power than FAIMS, and uses a steady or low frequency high voltage source, much simpler than the corresponding high frequency and high power FAIMS voltage source. The first description of a scheme to couple a DMA with a MS with high ion transmission and high resolution is contained in U.S. Pat. No. 5,869,831. While this patent teaches how to achieve high resolution and high ion transmission, an actual instrument able to attain high transmission with a resolving power exceeding 50 has not been reported in the 10 year period following patent application. This slow development has not been due to lack of interest in IMS-MS coupling. This point is evident from the commercial success of FAIMS, in spite of its complex power supply and limited resolving power. The slow development of DMA-MS coupling has been due in substantial measure to several serious technical difficulties. One initial geometrical problem is the fact that U.S. Pat. No. 5,869,831 gives no details on how to arrange the required pair of opposite conducting surfaces separated by insulating surfaces in a fashion avoiding gas leakage between these various parts, and offering very smooth surfaces to the flow so as to avoid turbulence transition at the high Reynolds numbers required for successful operation.

In order to tackle the geometrical problem, a distinction between various DMA types must be made. The type of symmetry exhibited by the DMA and whether or not it matches the symmetry of the MS to which it is to be coupled is important. The symmetry of the inlet hole to the MS is generally cylindrical (a round hole), while the specific DMA-MS high transmission coupling of U.S. Pat. No. 5,869,831 refers to a DMA with planar symmetry. With the exception of the radial DMAs of Flagan, et al. (1997) and of Pourprix (1992), the geometry of the exit region of the DMA (a straight slit or a circular slit) does not match that of the MS, whose inlet orifice has always been circular. We shall not be concerned here with radial DMAs, as they have never shown an ability to attain or even approach the resolving powers desirable for IMS. Subsequent considerations refer therefore to the more conventional family of so called "axial DMAs", where the gas flow enters into the analyzing portions of the instrument in a generally axial direction. U.S. Pat. No. 5,869,831 distinguishes between two kinds of axial DMAs: Those having a generally planar geometry, and those having a generally circular cross-section. The well-known principle of DMA operation is sketched in FIG. 1 for a planar DMA, where ions injected on a linear slit on the upper planar electrode (the inlet slit) are carried towards the right by the gas flow at velocity U, and towards the bottom by the electric field E at velocity ZE, such that the ion trajectories depend on the mobility Z, and only those ions having mobilities close to a special value Z* reach the sampling slit located on the lower planar electrode. The situation for cylindrical DMAs is similar, except that the two planar electrodes are substituted by coaxial cylinders, and the slits are now circular. The terms planar and cylindrical DMAs will be used in a loose sense. The plates do not need to be strictly parallel in the planar DMA. The electrodes could be curved in the plane of FIG. 1, while tending to be straight in the direction normal to the drawing. The slits will also be approximately straight. Similarly, the cylindrical DMA could more generally be axisymmetric, with walls curved in the plane of the figure. Although the "planar" and "cylindrical" DMAs are conceptually similar, their geometrical differences warranted a distinction and a separate treatment in U.S. Pat. No. 5,869,831, and the distinction will similarly be maintained here. Cylindrical DMAs have been considered in a companion application claiming equally the benefit of priority to U.S. Provisional Patent Application No. US60/790,679, filed on Apr. 10, 2006. The present invention will pursue the case of planar DMAs.

A first attempt at a solution to the geometrical problem noted was reported by Ude et al. (2004), as sketched in FIG. 2. Their design achieved the desired matching between the insulator and the conducting electrodes by constructing the electrodes out of thin metal sheet pieces supported by a system of thicker plates and screws on both sides of an insulating structure. This configuration could not be run at high speeds due to a variety of difficulties: first, due to gas leakage; second because small steps could not be avoided at points where the material forming the flow surface changed from a metal to an insulator; third, because the DMA electrodes were made out of thin metal sheet, which deformed at the desired high gas speeds due to considerable pressure differences between their inner and outer surfaces. In spite of these unresolved difficulties, the DMA was tested at moderate speeds, at which leaks and plate deformation levels were tolerable. Ude et al. (2004; see also Ude, 2004) then discovered that the resolving power of the DMA in this coupled DMA-MS system was considerably worse than the values previously demonstrated by a DMA alone. But the causes for this problem remained unclear. The purpose of this invention is therefore to solve both, the geometrical and the resolution difficulties previously identified.

A first point to notice in FIG. 2 is that the exit slit of the DMA coincides with the sampling hole of the MS, both being part of the same circular hole drilled in a metal piece at a point where it is relatively thin. In this arrangement analysis readily shows that the DMA resolution can be at most of the order of $(Q/q)^{1/2}$, where Q is the gas flow rate through the DMA and q is the gas flow rate sampled into the MS through the orifice, typically 0.5 lit/minute or more. In contrast, the resolution of a cylindrical DMA with a circular sampling slit, or that of a planar DMA with a linear sampling slit can be as high as Q/q, which is much larger than $(Q/q)^{1/2}$ when Q/q is large.

DESCRIPTION OF THE INVENTION

Figure 1:
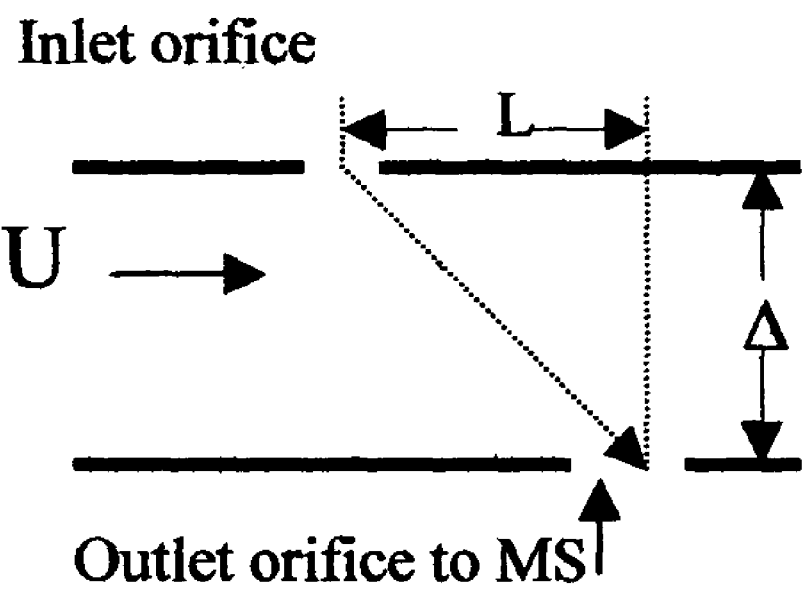
FIG. 1 is a sketch of a planar DMA with sheath gas coming from the left and an electric field driving downwards the ions entering through an inlet slit above and sampled through the sampling slit below
Figure 2:
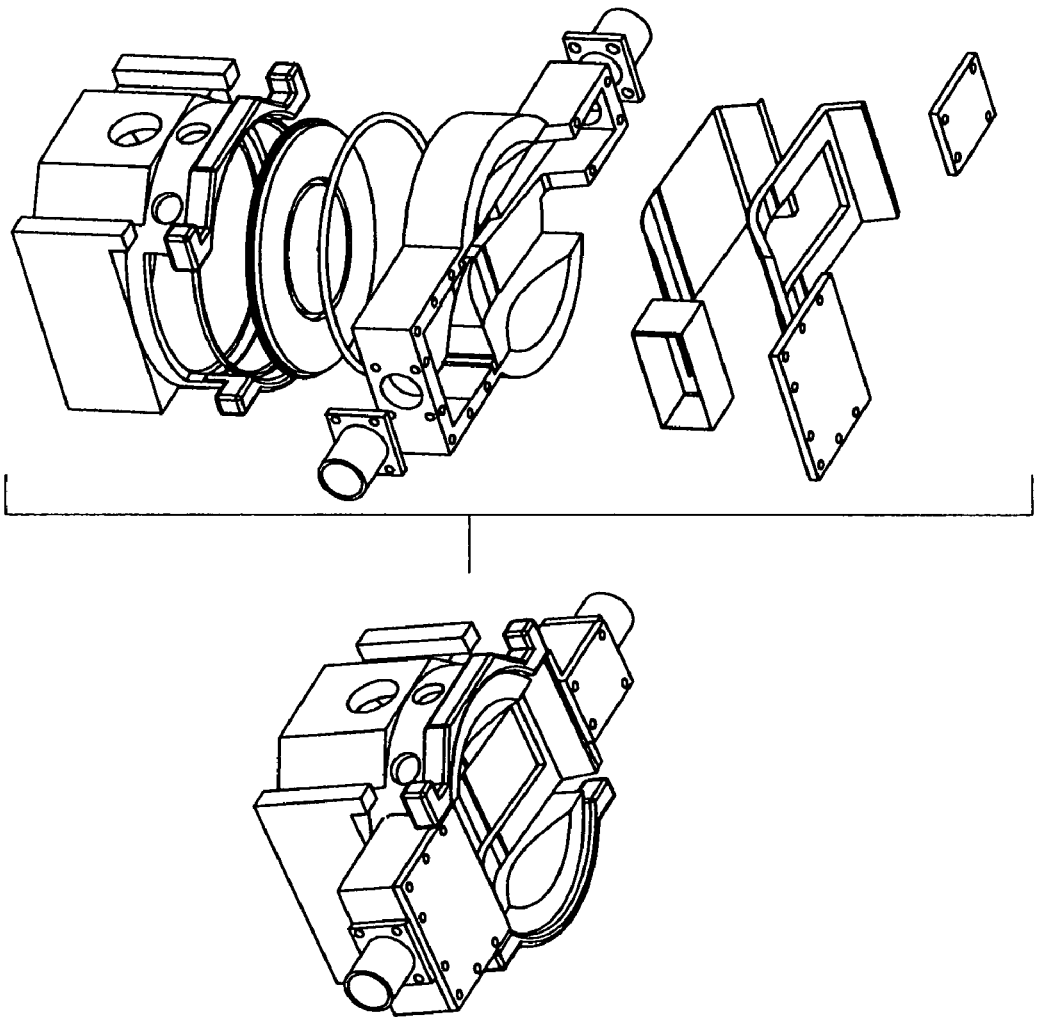
FIG. 2 shows a sketch of the coupling of Ude et al., (2004) between a planar DMA and Sciex's API-365 mass spectrometer (on the left)
Figure 3A:
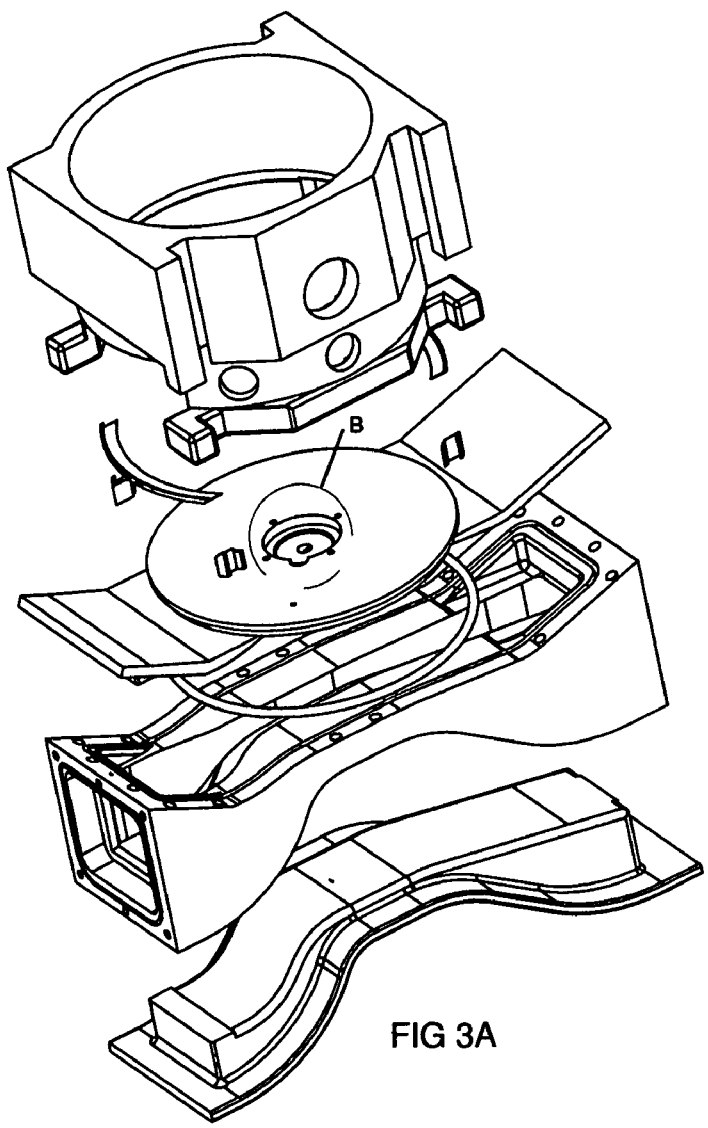
FIG. 3A shows the coupling of a planar DMA with a mass spectrometer through an elongated orifice having approximately the same shape on the DMA and on the MS ends
Figure 3B:
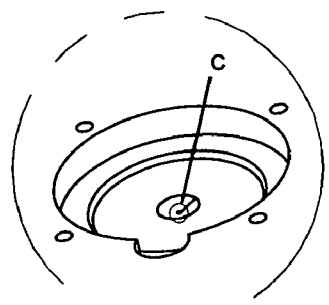
FIG. 3B shows a detail of FIG. 3A on the area where the elongated orifice connecting DMA and MS is located
Figure 3C:
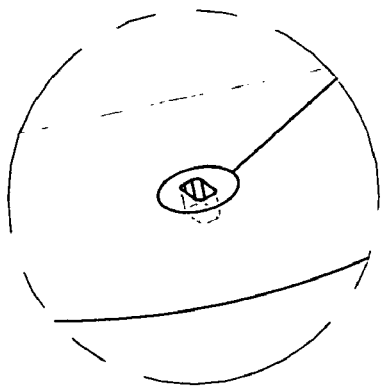
FIG. 3C shows in further detail this orifice, including hidden lines to appreciate its shape.

FIGS. 3A-C show a detail of one embodiment of the invention in a DMA with approximately planar geometry, where the exit slit of the DMA and the inlet orifice to the MS are both carved in a single plate, which is relatively thin in the region where the orifice is carved, so that the orifice geometry is almost the same on the DMA side and on the MS side. The orifice, however, is not circular, but elongated. Not shown in the figure are the details of the focusing and skimming system required downstream the orifice for the efficient transmission of the ions carried by this non-axisymetric jet. Note however that, far downstream, the flow field of a highly supersonic jet is relatively independent of the orifice geometry, provided that the downstream distance is large compared to the characteristic dimension of the hole (Fernández de la Mora, 1985; Fernandez de la Mora et al., 1990). This is due to the fact that, far downstream, the flow field is sensitive to the total mass flow and the distance to the orifice, but not to the details of the orifice shape, which looks effectively as a hole of infinitesimal dimensions. Consider for instance the substitution of a round orifice 250 μm in diameter by a rectangular slit with the same cross-sectional area, say 171 μm wide and 287 μm long. In the round orifice case, the free jet will remain supersonic over a distance downstream $x_D$ approximately equal to 0.67 times the square root of the ratio of pressures between upstream and downstream the hole (Ashkenas and Sherman). For a typical case where the upstream pressure is 1 atmosphere and the downstream pressure 1/760 atmospheres, $x_D$ is 18 times larger than the orifice diameter. In the elongated orifice case $x_D$ will be comparably long, and will therefore still be large compared to the wide dimension of the rectangular slit. This means that, for the moderately elongated hole under discussion, the axisymmetric lenses and skimming system of a conventional MS will transmit the ions with comparable efficiencies in the elongated and in the round orifice case. For substantially greater elongations of the orifice, modifications of the ion transmission system on the vacuum side would eventually become necessary. On the other hand, a modest reduction of the maximum slit width from 250 μm in the round orifice to 171 μm in the slightly elongated orifice leads to a considerable improvement of the resolving power of the DMA.

Figure 4A:
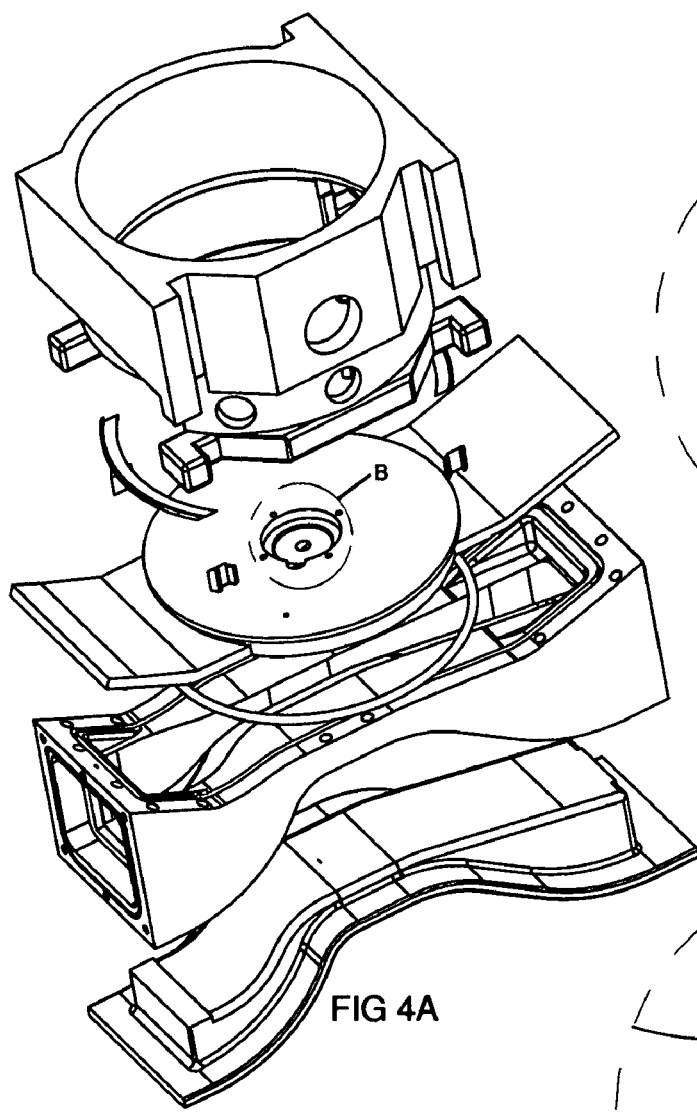
FIG. 4A shows the coupling of a planar DMA with a mass spectrometer through an orifice having a more elongated shape on the DMA end and a rounder shape on the MS end
Figure 4B:
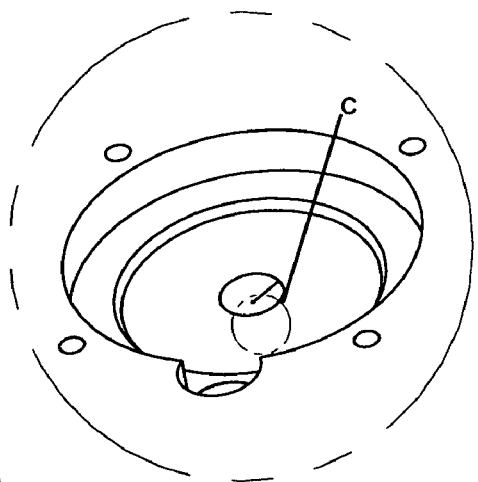
FIG. 4B shows a detail of FIG. 4A on the area where the deep orifice connecting DMA and MS is located
Figure 4C:
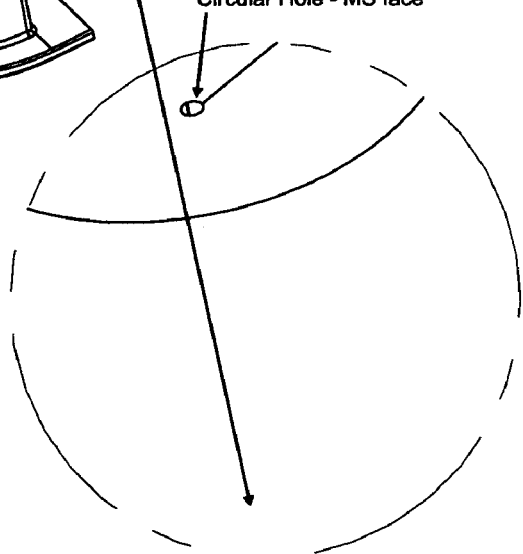
FIG. 4C shows in further detail this orifice including hidden lines to appreciate its shape evolution from one side to the other.

A detail of a second embodiment of the present invention is shown in FIGS. 4A-C. In this case, a plate thicker than that of FIG. 3A-C is used, enabling a smooth variation of the cross section of the hole as can be seen in detail in FIG. 4C, from a more circular shape on the MS end (top) to a more elongated geometry on the DMA end (bottom). This embodiment involves some losses of ions to the side walls of the relatively deep orifice, but the resulting reduction in ion transmission is compensated by an increase in DMA resolution following from the use of a longer and narrower slit, without the need to modify the ion transmission system on the vacuum end of the orifice. In the embodiment depicted in FIG. 4A, the means to transmit the ions from the DMA exit having a more elongated shape into the MS inlet having a more closely rounded form is a shaped perforation inside a conducting piece. The same purpose could be achieved by a tube made out of metal or another conducting material, by shaping it as a noncircular piece at least on one of its ends, while inserting it into the DMA electrode in a fashion such as to achieve a smooth flow surface and thereby avoid transition to turbulence of the DMA flow. Such a noncircular transfer tube is also considered part of the invention. Strictly speaking, it is not essential that this shaped transfer tube be made out of a conducting material. It can similarly be made out of glass or another insulator, as well as of a low conductivity material. The use of glass capillaries (rather than orifices drilled in metal parts) to transfer atmospheric ions into the vacuum system of a mass spectrometer has been taught by Labowsky et al. (1985). This system has been shown to be fairly effective in transmitting ions, and has the additional advantage of permitting the application of different electrical potentials at the entry and the exit of the capillary. This freedom to control independently these two voltages is also of interest in the coupling of a DMA with a MS. Consequently, insulating or low conductivity transfer lines between the DMA exit and the MS inlet are also incorporated into the invention.

Figure 5:
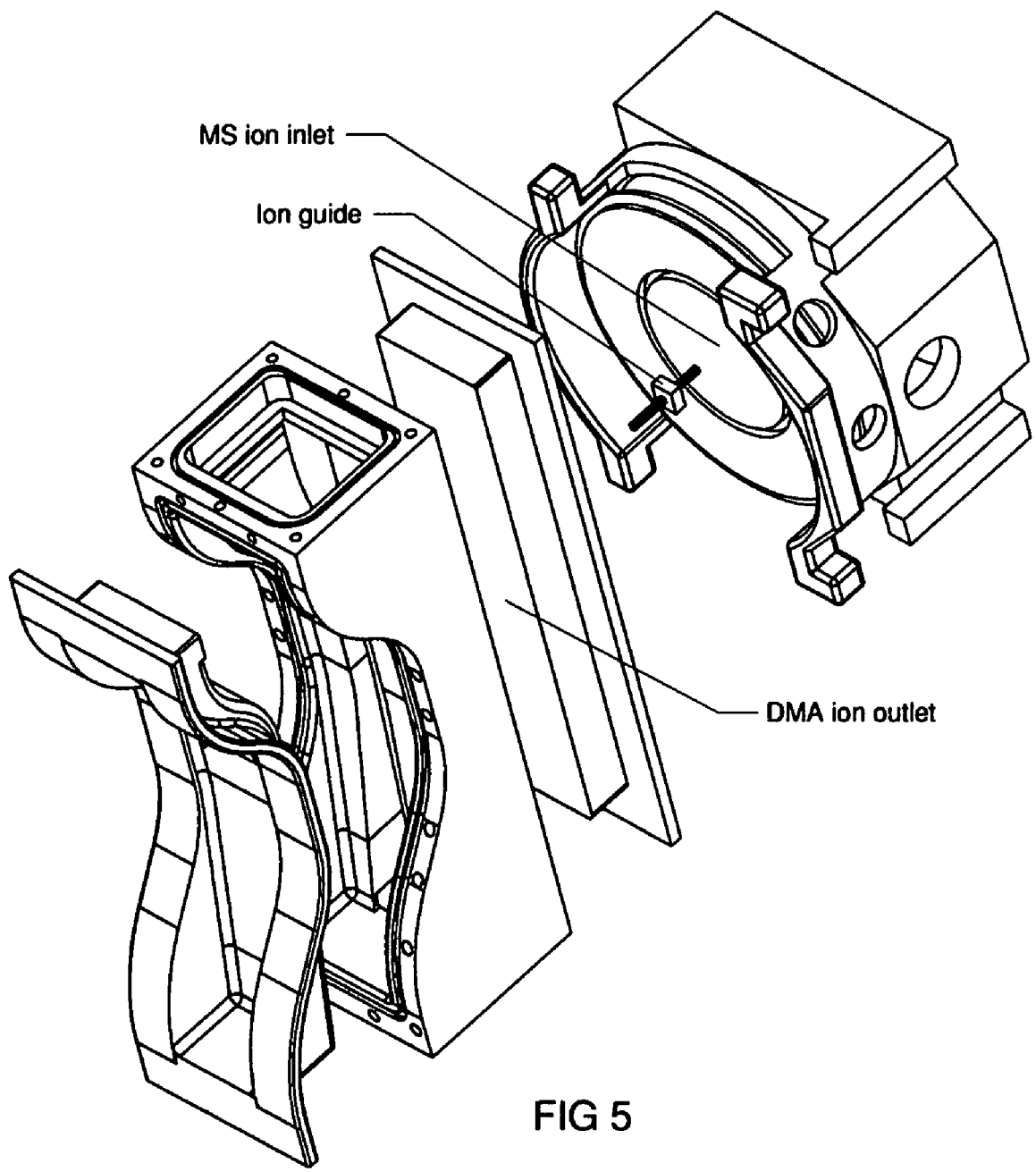
FIG. 5 shows schematically the coupling of a planar DMA with a mass spectrometer, where the DMA is built on a piece physically separated from the inlet orifice to the MS. Efficient ion transmission from one to the other is achieved by means of an ion guide using time varying electromagnetic fields that confine the ion beam and can in some cases even concentrate them enabling high transmission efficiency even when the sample flow to the MS is smaller than the exit flow of the DMA

A detail of a third embodiment of the invention is shown in FIG. 5. In this case the exit slit of the DMA is built on a piece physically separated from the inlet orifice to the MS. Efficient ion transmission from one to the other is achieved by means of an ion guide using time varying electromagnetic fields that confine the ion beam near the ion guide axis, and can in some cases concentrate them, enabling high transmission efficiency even when the sample flow into the MS is smaller than the ion flow exiting the DMA.

Another useful feature of this invention is a system to avoid the ingestion of humid or contaminated gas into the mass spectrometer. In APCI-MS this goal is conventionally achieved by introducing clean dry gas into a chamber located immediately upstream the inlet orifice of the mass spectrometer. Ions can be driven into the MS inlet against the countercurrent or curtain gas flow in this chamber by means of electric fields. But particles, drops, neutral gaseous contaminants and humidity are excluded by the counterflow gas from entering through the atmospheric pressure inlet to the MS. As previously noted among other places in U.S. Pat. Nos. 4,300,044 and 4,531,056, exclusion of humidity is important, as water vapor could otherwise condense on the ions in the free jet downstream the inlet orifice to the MS. Elimination of involatile contaminants is also desirable to avoid fouling of the DMA and the MS. The counterflow gas system to reject humidity and other contamination is therefore incorporated in one embodiment of this invention as part of the MS system. In this case, what we have termed the MS inlet would be the inlet to a curtain gas or counterflow chamber located immediately upstream the inlet orifice of the mass spectrometer. In another embodiment of the present invention, atmospheric contaminants and humidity are rejected not at the MS inlet, but at the inlet slit of the DMA. In this case the outlet of the DMA can be coupled directly to the atmospheric pressure inlet of the MS without the need of countercurrent gas in this region. A counterflow gas feature at the inlet slit of the DMA is not incorporated in most DMAs, including that of Labowsky and Fernández de la Mora (2006), where the inlet slit to the DMA brings outside gas into the interior of the DMA, whereby these impurities are retained in the sheath gas flow and can be passed into the mass spectrometer inlet. In one embodiment of the present invention, the inlet slit to the DMA carries clean flow from inside the DMA into the outside ion source region. Hence, neutral vapors, drops, particles and humidity existing in this outside region cannot enter into the DMA, while ions existing in this region can be driven by external electric fields against this countercurrent gas into the analyzing region of the DMA. A convenient way to control the outflow of countercurrent gas through the inlet slit to the DMA is to operate the DMA in closed loop, with its exhaust sheath gas being returned to its inlet sheath gas flow. Injection onto this loop of a net flow rate of clean gas equal to the flow rate q (counterflow) of ions sampled out of the DMA into the MS plus an extra flow rate q' ensures that the extra flow q' exits the inlet slit to the DMA as counterflow gas. Another known advantage of operating the DMA in closed loop is that the level of humidity can be controlled without drying the large flow of ambient air, which would otherwise need to be used as sheath gas.

A MORE DETAILED DESCRIPTION OF THE INVENTION

Figure 6:
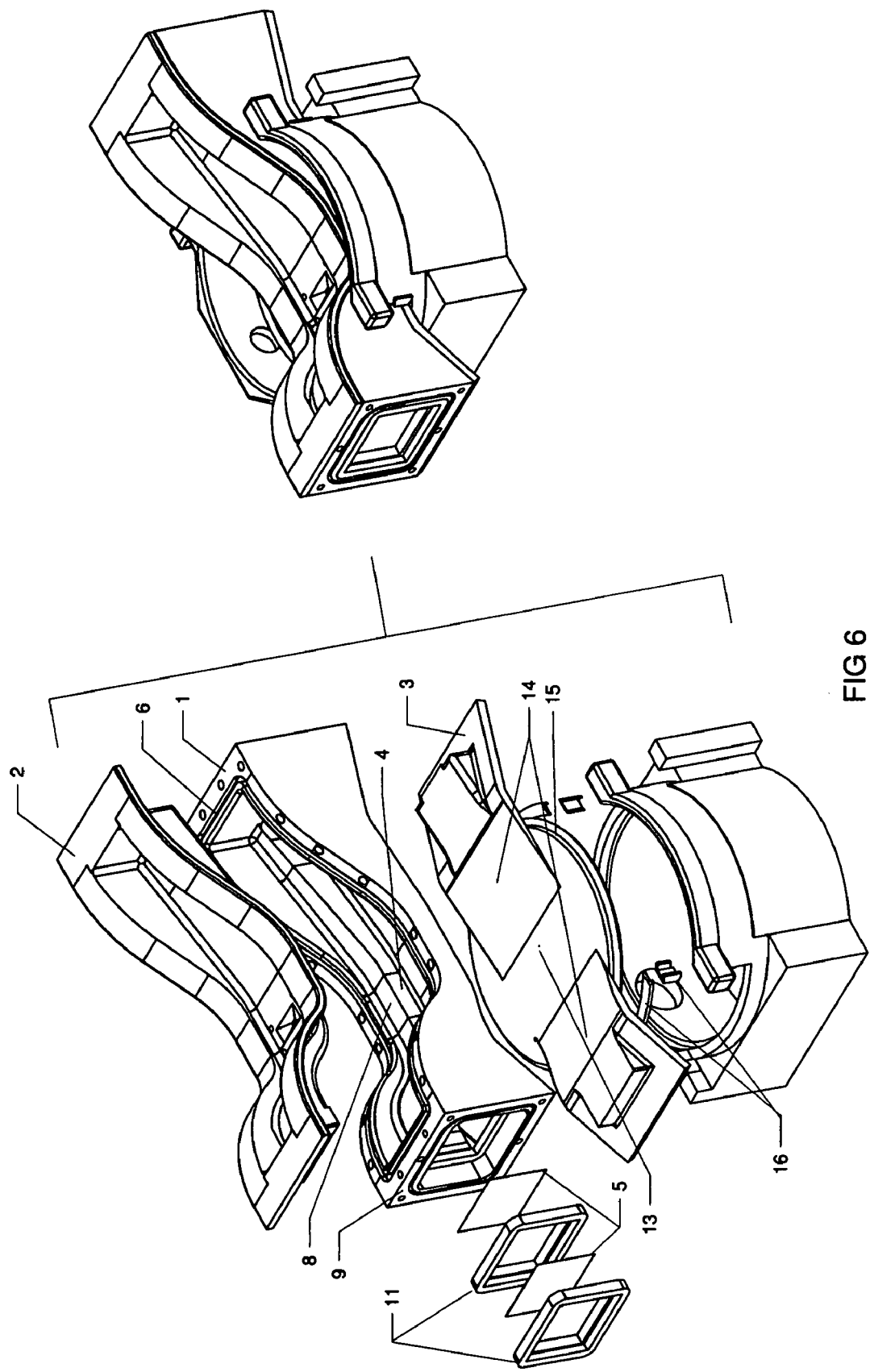
FIGS. 6-8 show more detail of a DMA with planar symmetry and its coupling to a MS
Figure 7:
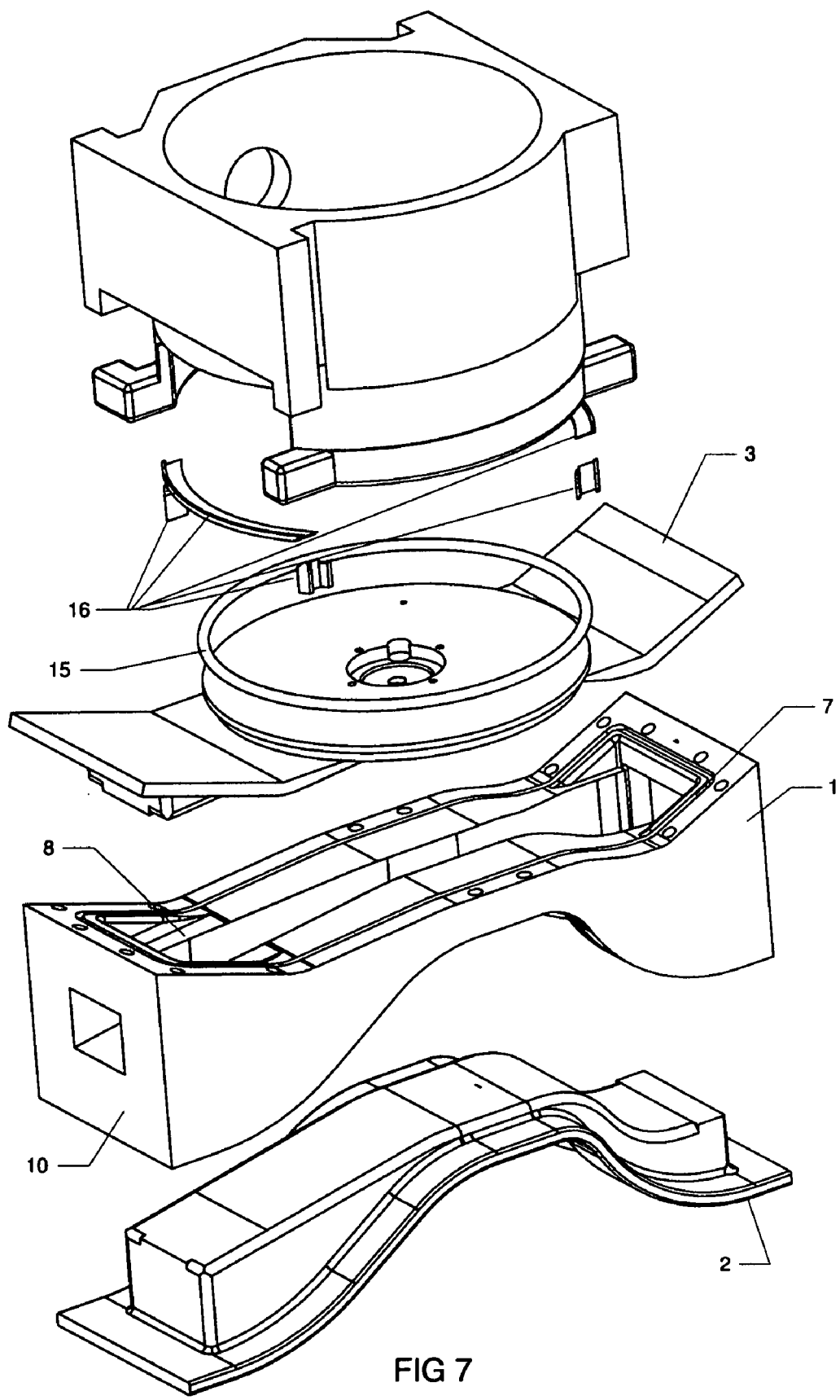
Figure 8:
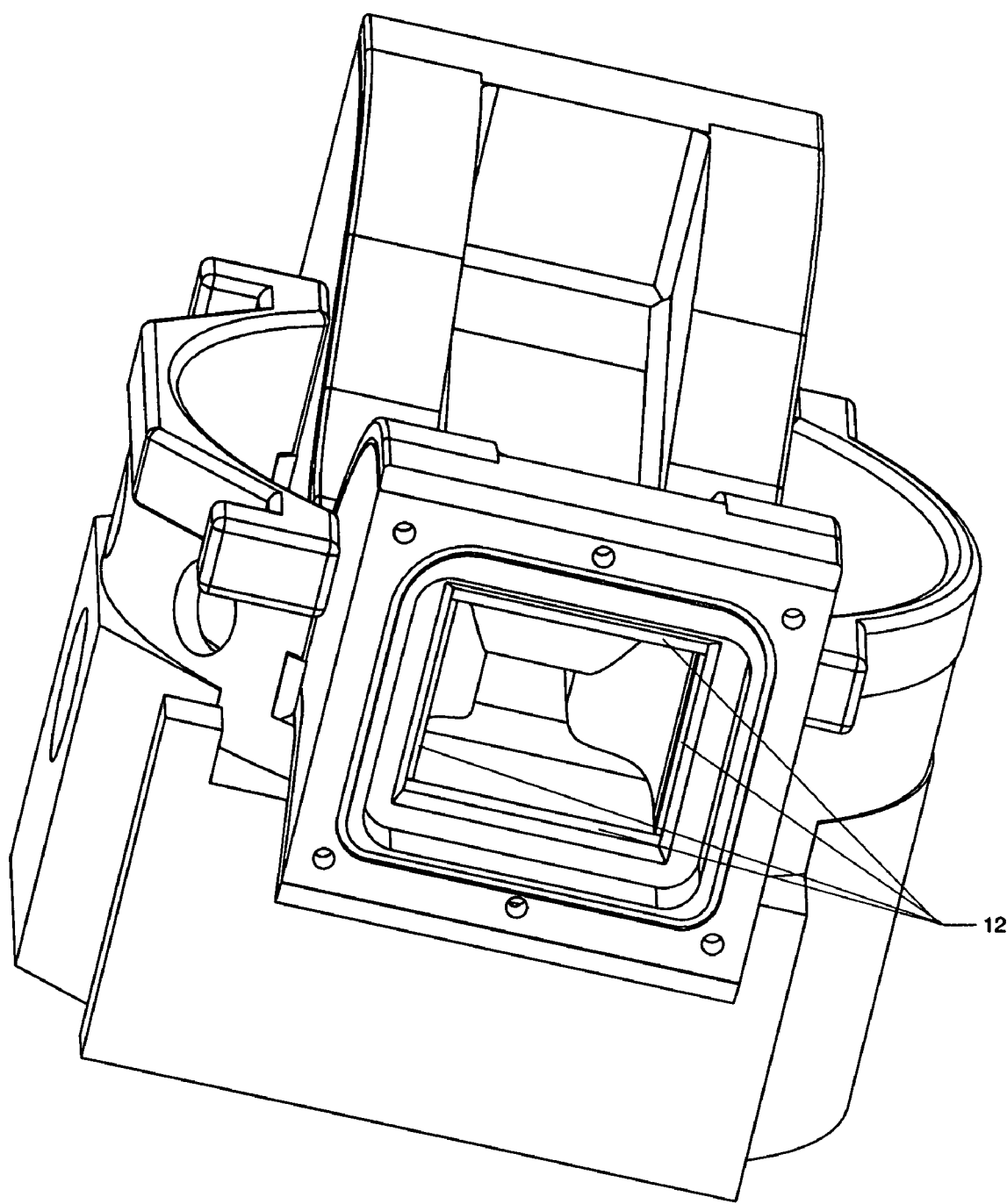

A more detailed description of a DMA with planar symmetry and of its coupling to a MS is shown in FIGS. 6-8. The specific design depicted is appropriate for coupling a DMA to several widely used mass spectrometers commercialized by the company Sciex. The distance $\Delta$ between the opposite planar electrodes is in this case 10 mm, and the axial distance L between the inlet and the outlet slits is 20 mm. The region between the inlet and the outlet slits, where the ions separate according to mobility, will be referred to as the working section of the DMA. This working section is rectangular, is preceded upstream by a converging region that contributes to the laminarization process, and is followed downstream by a slowly diverging region acting as a diffuser to minimize pressure drop. The particular embodiment shown has demonstrated a resolving power in the range of 100 with ions having an electrical mobility of 1.79 $cm^2/V/s$ in air. The DMA exit slit width was of 175 µm, which is substantially smaller than the original inlet orifice to the MS (250 µm in diameter). This excellent performance has been attained with a slit fabricated in a thin plate, whereby its geometry is identical on the MS and the DMA sides. In the embodiment of FIGS. 6-8, the working section has a rectangular cross section width a height $\Delta$ of 10 mm and width w of 17.5 mm. This width is of course the distance between the side insulating ends of the supporting box ([1] in FIG. 6). A with w larger than the characteristic length $\Delta$ has been chosen to reduce possible stray fields associated to ions accidentally deposited on the side insulating walls, since such uncontrolled fields could displace laterally the position of the ions. An alternative means to compensate for this possible lateral displacement is to use a wider ion inlet slit to the DMA than the corresponding DMA outlet slit, as previously done by Ude et al. (2004). This additional precaution allows reducing the DMA width w to a value closer to the distance $\Delta$ between electrodes, and this permits reducing the flow rate of sheath gas without loss of resolution.

Those skilled in the art of mechanical and fluid dynamical design could readily modify the structure illustrated in FIGS. 6-8 to couple a similar DMA to other mass spectrometers having different configurations for the atmospheric pressure interface piece. No prior solution has been given to the problem of rigidly coupling two metallic electrodes [2] and [3] held at different potentials while avoiding gas leakage through the junctions, yet providing a structure with sufficient rigidity to withstand substantial pressure differences. Note in this respect that when the fluid velocity is sonic at the minimum cross section of the DMA [4] and the pressure there is kept close to atmospheric conditions, the pressure at the inlet region near the laminarization screens [5] approaches 2 atmospheres. The prototype tested built according to FIGS. 6-8 is leak free, and sufficiently rigid to suffer negligible deformation even at high speed. It has in fact been tested up to Mach numbers exceeding 0.6. The DMA is kept leak tight by means of a parallelepiped-shaped supporting box made of an insulating material [1], which supports on its upper and lower open faces the two main DMA electrodes. Tightness at the junction of these two electrodes with the open insulating box is attained by means of viton o-rings through an external closed circuit around the box ([6] in FIG. 6 and [7] in FIG. 7), while the inner contact [8] between the pieces encloses the flow. The careful inner, upper and lower three-dimensional (3D) machining of the box [1], matched by the machining of the electrodes, defines the flow path based on classical wind-tunnel design. It is aimed at providing a steady laminar flow at the working section, with higher inlet accelerations than in conventional wind tunnel design. The front [9] and back [10] faces of the insulating box are also open to enable entry and exhaust of the clean DMA gas flow. Laminarization screens [5] are inserted at the entry and trapped and tightened by insulating framing pieces [11]. To avoid discontinuities in the wet (bathed by the flow of sheath gas) surfaces that could lead to steps and precipitate transition to turbulence, the laminarization screen located most downstream sits directly on the two electrodes and the side walls of the supporting box [12], which define the rest of the DMA flow-path until the exhaust. Discontinuities at the exhaust are not critical. Note in FIGS. 6-8 the peculiarly shaped electrode supporting the orifice [13], too small to be appreciable in the figure. This surface would have preferably been flat, as shown, for instance in the model of FIG. 5, where the DMA surfaces are designed without constraints associated to the need to match the geometry of the MS inlet piece. However, the requirements of fitting the DMA shape to an existing MS inlet piece forces certain limitations, while further limitations are imposed by the requirement of avoiding discontinuities in the wet surfaces. In the embodiment of FIG. 6, the depth of the orifice [13] from the DMA outlet to the MS inlet is the same as in the original Sciex MS, and this forces a non-ideal aerodynamic shape on the MS side of this electrode: the electrode there needs to gain some thickness (say 5 mm) from the ion exhaust. That growth is achieved via smoothly machined curves [14] situated in the region where the positive acceleration effect due to cross-sectional change created by the three other surfaces enclosing the flow path is strong enough to overwhelm the negative effects of the fourth, undesirably-growing surface. These curves and the overall behavior of the flow have been numerically simulated and optimized at the fore part of the flow, between the last laminarization screen and the ion exhaust orifice [13]. The design has been successful as demonstrated by the high resolution attained. In another embodiment, the surfaces [14] may be made aerodynamically more favorable by increasing the depth of the inlet orifice to the MS. As already noted, this approach leads to some loss of ions on the orifice walls, reducing the ion transmission, but enables a DMA sampling slit more elongated than the MS inlet slit. Leak tight coupling to the MS is done with an o-ring [15] similar to that existing in the original Sciex's MS. Electrical insulation required between the DMA electrode containing the MS inlet hole and the main body of the MS is achieved with the original insulation system of Sciex's MS complemented with several additional insulating parts [16].

Most parts of the prototype have been fabricated in a milling machine. The fitting between the supporting box [1] and the electrodes [2, 3] uses fillets with large radiuses, to allow the use of large milling cutters and decrease machining times. However, a flat-head tool with small radius needs to be used to get sharp edges at the flow entry ([12] in FIG. 8), where the laminarization screen sits. Die sinking electrical discharge machining (EDM) is used to provide small, controlled local thickness at the ion inlet and exhaust regions. Wire EDM is used for the cut-outs of the ion inlet and outlet, which requires prior drilling of a hole slightly wider than the wire.

We have stressed the importance of high ion transmission efficiency from an ion source (say an electrospray source) through the DMA into the MS inlet. Much emphasis has been given to high transmission at the DMA outlet and at its connection to the MS. Equally important is to achieve high transmission at the ion inlet slit to the DMA. This high transmission is necessary also when implementing the counterflow scheme already discussed to avoid ingestion of contaminants at this inlet slit. The present invention incorporates a system to achieve this goal based on allowing penetration through the full depth of the inlet slit of the electric fields existing both inside and outside this slit. This objective is possible only if the depth of the slit is small relative to its width, or at most comparable to it. FIG. 6 shows a concrete implementation of this principle in the recess made on the outer surface of the electrode [2] supporting the inlet slit. The figure also shows two (out of four) orifices at the corners of the rectangular base of this pyramidal recess, which are threaded and permit installation of a leak-tight charging chamber in the vicinity of the sampling slit. This charging chamber is provided with an inlet and an outlet tube to pass through it a purge or sample gas, and serves multiple purposes. It can be used as an electrospray ionization (ESI) chamber by providing means to introduce liquid through a capillary needle as well as to charge the liquid meniscus to a high voltage. In particular, one can locate the tip of the electrospray needle relatively close the ion inlet slit, so that the intensity of electrospray ions can be large, and the relatively large associated electric field present propels effectively these ions against the countercurrent gas coming through the slit from the interior of the DMA. This electrospray can be used to directly introduce solution ions into the DMA, as in conventional electrospray mass spectrometry. It can alternatively be used to charge volatile substances introduced from the ambient into the chamber, where they are ionized by the electrospray ions and drops. For example, electrospraying acidified water inside this chamber leads to effective protonation of polar volatile species. For the purpose of monitoring volatile vapors, the charging chamber does not need to necessarily contain an electrospray source. It could contain (or allow passage of) other alternative ionization sources, such as an electrical discharge, a radioactive source, a photo-ionization source, etc. Another advantage of this leak-tight charging chamber is that it permits simultaneous control of the countercurrent gas flow and the sample flow of atmospheric vapors being monitored. We have noted that the counterflow gas is easily controlled if the DMA circuit (including the pump) is closed and free from leaks. However, powerful and inexpensive vacuum cleaner pumps are rarely leak-tight, and operating under closed circuit at high DMA velocities is complicated due to heating of the gas while going through the pump. A simpler alternative is to sample filtered (and perhaps dried) room air at the sheath gas inlet to the DMA, in which case the ion inlet slit will operate at reduced pressure (particularly so at high DMA velocities). Nonetheless, one can easily control the input sample gas into the ES chamber and the exit sample gas out of the charging chamber into a small suction pump with a pair of valved flowmeters located at the inlet and outlet tubes of the charging chamber. This charging chamber and its operational advantages are also considered part of the invention

We claim:

1. A method of transmitting gas carrying mobility-selected ions from the ion exhaust of a DMA with approximately planar symmetry into an inlet orifice of an analytical instrument, the method including:
    providing a DMA with approximately planar symmetry and a non-circular exhaust;
    arranging said non-circular exhaust such that a gas carrying mobility-selected ions emitted from said non-circular exhaust is directed towards an inlet orifice of an analytical instrument; and
    operating said DMA to cause a gas carrying mobility-selected ions to emit from said non-circular exhaust towards said inlet orifice of said analytical instrument.

2. A method according to claim 1 where said inlet orifice has a non-circular cross-section.

3. A method according to claim 1 where said mobility-selected ions exiting said ion exhaust of said DMA are transmitted to said inlet orifice of said analytical instrument by a transfer line connecting on its upstream region with said non-circular exhaust of said DMA, and connecting on its downstream region with said inlet orifice of said analytical instrument, where
    (i) said upstream region is more elongated than said downstream region
    (ii) and the flow is not restricted within said more elongated upstream region of said transfer line but rather within either said downstream region of said transfer line, or at the exit of said transfer line, or downstream from said transfer line.

4. A method according to claim 1 where said mobility-selected ions exiting said non-circular exhaust of said DMA with approximately planar symmetry are transmitted by an ion guide to said inlet orifice of said analytical instrument, where the flow sampled into said inlet orifice is not limited upstream from it, so that the ion guide operates at a pressure close to that prevailing between the inlet and outlet slits of the DMA.

5. A method according to claim 1 where two interior surfaces of said DMA with approximately planar symmetry are formed by two conducting electrodes closing without substantial gas leakage two opposite open areas of an electrically insulating box-shaped structure, such that there is at least one junction between an upstream wetted surface on said insulating box-shaped structure and an adjacent downstream wetted surface of at least one of said conducting electrodes.

6. A method according to claim 5 where flow instabilities normally produced as the sheath gas transits through said at least one junction are avoided by placing a laminarization screen at said at least one junction, pressing tightly against one of said conducting electrodes, such that said wetted surface of said one of said conducting electrodes located downstream from said screen does not offer discontinuities to the flow.

7. An approximately planar DMA apparatus to separate ions according to their electrical mobility, comprising:
   i) a box-shaped insulating structure with several wide openings, including an open top surface and an open bottom surface;
   ii) a top conducting electrode closing said top open surface, and a bottom conducting electrode closing said bottom open surface; and
   iii) a first sealing gasket placed between said top conducting electrode and said top open surface, and a second sealing gasket placed between said bottom conducting electrode and said bottom open surface, such that substantial leakage of gas through the union of said insulating box and said conducting electrodes is avoided.

8. An apparatus according to claim 7 including one junction between an upstream wetted surface on said insulating box and an adjacent downstream wetted surface on at least one of said conducting electrodes, where flow instabilities normally produced as the sheath gas transits through said junction are avoided by (i) placing a laminarization screen at said junction; (ii) pressing tightly said screen against said at least one conducting electrode, such that said wetted surface of said at least one conducting electrode located downstream from said screen does not offer discontinuities to the flow.

9. An apparatus according to claim 8 incorporating an elongated outlet orifice on said bottom conducting electrode.

10. An apparatus according to claim 7 operated in tandem with an analytical instrument.

11. An apparatus according to claim 10 where said ions enter into said analytical instrument through a noncircular orifice.

12. An approximately planar DMA including a shaped ion outlet conduit, said conduit having an entry section more elongated than its exit section, where the cross sectional area of said more elongated entry section is larger than the cross sectional area of said exit section, such that the flow does not become sonic within said more elongated entry section.

13. The approximately planar DMA of claim 12 coupled to a mass spectrometer.

14. A method according to claim 3, wherein said transfer line is defined in an electrode of said DMA.

15. A method according to claim 14, wherein said analytical instrument is an API-MS.

* * * * *